US009530238B2

(12) United States Patent
Inoue (10) Patent No.: US 9,530,238 B2
(45) Date of Patent: Dec. 27, 2016

(54) IMAGE PROCESSING APPARATUS, METHOD AND PROGRAM UTILIZING AN OPACITY CURVE FOR ENDOSCOPIC IMAGES

(71) Applicant: FUJIFILM Corporation, Tokyo (KR)

(72) Inventor: Tsutomu Inoue, Tokyo (KR)

(73) Assignee: FUJIFILM CORPORATION, Tokyo (JP)

( * ) Notice: Subject to any disclaimer, the term of this patent is extended or adjusted under 35 U.S.C. 154(b) by 104 days.

(21) Appl. No.: 14/289,542

(22) Filed: May 28, 2014

(65) Prior Publication Data
US 2014/0267269 A1 Sep. 18, 2014

Related U.S. Application Data

(63) Continuation of application No. PCT/JP2012/007616, filed on Nov. 28, 2012.

(30) Foreign Application Priority Data

Nov. 30, 2011 (JP) ................................. 2011-261885

(51) Int. Cl.
*G06T 15/08* (2011.01)
*A61B 6/03* (2006.01)
(Continued)

(52) U.S. Cl.
CPC ............... *G06T 15/08* (2013.01); *A61B 6/032* (2013.01); *A61B 6/466* (2013.01); *A61B 6/50* (2013.01);
(Continued)

(58) Field of Classification Search
CPC ................................. G06T 15/08; G06T 19/003
See application file for complete search history.

(56) References Cited

U.S. PATENT DOCUMENTS 6,380,958 B1 * 4/2002 Guendel ................. G06T 15/20
345/427
2004/0259065 A1 * 12/2004 Geiger ..................... G06T 5/009
434/272
(Continued)

FOREIGN PATENT DOCUMENTS

EP 2372661 A2 10/2011
JP 2006-055402 A 3/2006
(Continued)

OTHER PUBLICATIONS

Extended European Search Report dated Jun. 25, 2015.
(Continued)

*Primary Examiner* — Daniel Hajnik
(74) *Attorney, Agent, or Firm* — McGinn IP Law Group, PLLC.

(57) ABSTRACT

When a virtual-endoscopic-image is generated from a three-dimensional-image representing a tubular-organ, a predetermined range is set in the vicinity of a viewpoint set in advance in the three-dimensional-image, and each of a lumen-region and a wall-region of the tubular-organ in the set range is identified. A voxel-value or a voxel-value-interval constituting a boundary between a range of voxel values in the identified lumen-region and a range of voxel values in the identified wall-region is obtained based on information about voxel-values in the identified lumen-region and information about voxel-values in the identified wall-region, and an opacity-curve representing a relationship between voxel values and opacity is set in such a manner that the opacity changes from a value representing a transparent-state to a value representing an opaque-state at the voxel-value or in the voxel-value-interval. The virtual-endoscopic-image is generated from the three-dimensional-image by volume rendering using the set viewpoint and the set opacity-curve.

14 Claims, 5 Drawing Sheets

(51) Int. Cl.
    *A61B 6/00*     (2006.01)
    *G06T 19/00*     (2011.01)
    *G06T 15/06*     (2011.01)
    *G06T 15/50*     (2011.01)
    *G06T 19/20*     (2011.01)

(52) U.S. Cl.
    CPC ............. *A61B 6/5217* (2013.01); *G06T 15/06* (2013.01); *G06T 15/50* (2013.01); *G06T 19/003* (2013.01); *G06T 19/20* (2013.01); *G06T 2210/41* (2013.01)

(56) References Cited

U.S. PATENT DOCUMENTS

| | | | | |
|---|---|---|---|---|
| 2005/0119550 | A1* | 6/2005 | Serra | G06T 19/00 600/407 |
| 2010/0185094 | A1* | 7/2010 | Hamada | A61B 8/14 600/443 |
| 2011/0242097 | A1 | 10/2011 | Miyamoto | |

FOREIGN PATENT DOCUMENTS

| | | |
|---|---|---|
| JP | 2007-044121 A | 2/2007 |
| JP | 2010-284313 A | 12/2010 |
| JP | 2011-212219 A | 10/2011 |

OTHER PUBLICATIONS

International Search Report (ISR) (PCT Form PCT/ISA/210), in PCT/JP2012/007616, dated Feb. 5, 2013.

B. L. Odry et al., "Active contour approach for accurate quantitative airway analysis", Medical Imaging 2008: Physiology, Function, and Structure from Medical Images, Proceedings of SPIE—Int'l, Society for Optical Engineering, vol. 6916, pp. 691613-1-691613-11, 2008.

* cited by examiner

IMAGE PROCESSING APPARATUS, METHOD AND PROGRAM UTILIZING AN OPACITY CURVE FOR ENDOSCOPIC IMAGES

CROSS-REFERENCE TO RELATED APPLICATIONS

This application is a Continuation of PCT International Application No. PCT/JP2012/007616 filed on Nov. 28, 2012, which claims priority under 35 U.S.C. §119(a) to Japanese Patent Application No. 2011-261885 filed on Nov. 30, 2011. Each of the above application(s) is hereby expressly incorporated by reference, in its entirety, into the present application.

BACKGROUND OF THE INVENTION

1. Field of the Invention

The present invention relates to an image processing apparatus, method and program that generates a virtual endoscopic image from a three-dimensional image representing a tubular organ.

2. Description of the Related Art

In recent years, high quality three-dimensional images representing subjects became obtainable by an advance in modalities, such as a multi-slice CT. Consequently, medical image processing techniques for generating pseudo-three-dimensional images are also being developed. A virtual endoscopic display method is an example of such techniques. In the virtual endoscopic display method, a viewpoint is set within a lumen, and a perspective projection image is generated based on the viewpoint, and displayed. When a user successively changes the viewpoint in virtual endoscopic display, virtual endoscopic display can provide images as if they are imaged by a camera of an endoscope moving in the inside of the body.

As a method for generating a virtual endoscopic image, a volume rendering method is known. In the volume rendering method, an image is visualized by assigning opacity and chromaticity to a three-dimensional image, and by performing ray-casting. When a virtual endoscopic image is generated by this volume rending method, it is necessary to appropriately set an opacity curve representing a relationship between voxel values and opacity in such a manner that the opacity of "0" is assigned to a part corresponding to a lumen, in which a viewpoint is positioned, and the opacity of "1" is assigned to a part corresponding to a wall.

Meanwhile, when a tubular organ to be observed is a bronchus or bronchi, a blood vessel or vessels, or the like, the tubular structure gradually becomes thinner toward its peripheral end, and voxel values at a root part of a lumen and voxel values at a peripheral part of the lumen greatly differ from each other. Therefore, if a virtual endoscopic image is generated by using the same opacity curve for the root part and for the peripheral part, the inner wall of the lumen may be displayed at the root part. However, there is a problem that it is impossible to display the inner wall of the lumen at the peripheral part.

To solve this problem, Japanese Unexamined Patent Publication No. 2011-212219 (Patent Document 1) proposes setting an opacity curve at a changed viewpoint position when virtual endoscopic images are generated and displayed while a viewpoint position is sequentially changed. When a histogram of voxel values in a region surrounding a viewpoint position before change is HD(v), using a voxel value as variable v, and a histogram of voxel values in a region surrounding a viewpoint position after change is Hn(v), a degree of similarity between a histogram represented by HD(v−x) and histogram Hn(v) is calculated while the value of x is changed. Further, the value of x when the degree of similarity is the highest is determined as movement amount m. Further, opacity curve O(v) (=OD(v−m)), which is obtained by moving opacity curve OD(v) at the viewpoint position before change by movement amount m, is set as the opacity curve at the viewpoint position after change.

SUMMARY OF THE INVENTION

However, the histogram of voxel values in a surrounding region of the viewpoint position represents the entire region located in the surrounding region of the viewpoint position. In other words, the histogram represents the distribution of all voxel values in a lumen region and a wall region of a tubular organ that are located in the surrounding region of the viewpoint position and the other regions located in the surrounding region of the viewpoint position together. Therefore, it is difficult to accurately obtain a boundary between the range of voxel values in the lumen region and the range of voxel values in the wall region from this histogram. Hence, the method of Patent Document 1, in which an opacity curve is set based on this histogram, has a problem that it is impossible to set an appropriate opacity curve in which the opacity of "0" is assigned to the lumen region and the opacity of "1" is assigned to the wall region. This problem is significant especially when a difference between voxel values in the lumen region and voxel values in the wall region is small.

In view of the foregoing circumstance, it is an object of the present invention to provide an image processing apparatus, method and program that can set, for each viewpoint, an opacity curve appropriate for observation of a tubular organ at the position when a virtual endoscopic image is generated from a three-dimensional image representing the tubular organ.

An image processing apparatus according to the present invention is an image processing apparatus that generates a virtual endoscopic image from a three-dimensional image representing a tubular organ, the apparatus comprising:

a region identification means that sets, in the three-dimensional image, a predetermined range in the vicinity of a viewpoint that has been set in advance, and identifies each of a lumen region and a wall region of the tubular organ in the set range;

an opacity curve setting means that obtains, based on information about voxel values in the identified lumen region and information about voxel values in the identified wall region, a voxel value or a voxel value interval constituting a boundary between a range of voxel values in the identified lumen region and a range of voxel values in the identified wall region, and sets an opacity curve representing a relationship between voxel values and opacity in such a manner that the opacity changes from a value representing a transparent state to a value representing an opaque state at the voxel value or in the voxel value interval; and a virtual endoscopic image generation means that generates the virtual endoscopic image from the three-dimensional image by volume rendering using the set viewpoint and opacity curve.

In the image processing apparatus, the predetermined range may be a visual field range determined based on the set viewpoint, an observation direction and a visual field angle. Alternatively, the predetermined range may be a region within a certain distance from the set viewpoint, as the center of the region.

When the range of voxel values in the lumen region and the range of voxel values in the wall region overlap with each other, the opacity curve setting means may obtain the overlapping value or interval, as a voxel value or a voxel value interval constituting the boundary. Alternatively, the opacity curve setting means may obtain a voxel value (the voxel value of the largest) at which a number of voxels represented on a vertical axis is the largest in a histogram of a lumen region and a voxel value (the voxel value of the largest) at which a number of voxels represented on a vertical axis is the largest in a histogram of a wall region. Further, the opacity curve setting means may obtain, based on the voxel values of the largest, a voxel value or a voxel value interval constituting a boundary between a range of voxel values in the lumen region and a range of voxel values in the wall region.

The opacity curve setting means may set an opacity curve in such a manner that opacity gradually changes from a value representing a transparent state to a value representing an opaque state in the voxel value interval. Alternatively, the opacity curve setting means may set an opacity curve in such a manner that opacity changes stepwise from a value representing a transparent state to a value representing an opaque state at a point in the voxel value interval.

When the opacity curve setting means sets an opacity curve in such a manner that opacity gradually changes from a value representing a transparent state to a value representing an opaque state in a voxel value interval in which the range of voxel values in the lumen region and the range of voxel values in the wall region overlap with each other, the opacity curve setting means may determine the inclination of the opacity curve at each point in the voxel value interval based on the form of a histogram of voxel values in the lumen region and the form of a histogram of voxel values in the wall region in the overlapping voxel value interval.

Further, the opacity curve setting means may store a base viewpoint and an opacity curve at the base viewpoint, and set a tolerable amount of change in opacity in such a manner that the tolerable amount is smaller as a distance, along the direction of a course of the tubular organ, between the set viewpoint and the base viewpoint is shorter, and set an opacity curve at the set viewpoint in such a manner that a difference between an opacity value in the opacity curve at the set viewpoint and an opacity value in the opacity curve at the base viewpoint corresponding to a same voxel value does not exceeds the set tolerable amount of change.

Here, the base viewpoint may be a predetermined initial viewpoint, or a viewpoint before change when the position of a viewpoint has been changed.

The image processing apparatus may further include a CPR image generation means that sets, based on voxel values in the predetermined range, a window level and a window width, and generate a CPR image representing the tubular organ from the three-dimensional image by using the set window level and window width.

The image processing method of the present invention is a method in which processing performed by each of the means of the image processing apparatus is performed by at least one computer.

The image processing program of the present invention is a program for causing at least one computer to perform the image processing method. The program is recorded on a recording medium, such as a CD-ROM and a DVD, or recorded in a storage attached to a server computer or a network storage in a downloadable state, and provided for a user.

In the image processing apparatus, method and program of the present invention, when a virtual endoscopic image is generated from a three-dimensional image representing a tubular organ, a predetermined range is set in the vicinity of a viewpoint that has been set in advance in the three-dimensional image, and each of a lumen region and a wall region of the tubular organ in the set range is identified. Further, a voxel value or a voxel value interval constituting a boundary between a range of voxel values in the identified lumen region and a range of voxel values in the identified wall region is obtained based on information about voxel values in the identified lumen region and information about voxel values in the identified wall region. An opacity curve representing a relationship between voxel values and opacity is set in such a manner that the opacity changes from a value representing a transparent state to a value representing an opaque state at the voxel value or in the voxel value interval. The virtual endoscopic image is generated from the three-dimensional image by volume rendering using the set viewpoint and opacity curve. Therefore, it is possible to accurately obtain, for each viewpoint, a boundary between the range of voxel values in the lumen region and the range of voxel values in the wall region in the vicinity of the viewpoint. Therefore, it is possible to set an opacity curve appropriate for observation of a tubular organ at the viewpoint position.

In the image processing apparatus, method and program of the present invention, when the predetermined range is a visual field range determined based on the set viewpoint, an observation direction and a visual field angle, it is possible to set an opacity curve dependent on information about voxel values in a region to be displayed by a virtual endoscopic image. Therefore, it is possible to provide a virtual endoscopic image more appropriate for observation of a tubular organ.

Further, the step of setting an opacity curve may store a base viewpoint and an opacity curve at the base viewpoint, and set a tolerable amount of change in opacity in such a manner that the tolerable amount is smaller as a distance, along the direction of a course of the tubular organ, between the set viewpoint and the base viewpoint is shorter, and set an opacity curve at the set viewpoint in such a manner that a difference between an opacity value in the opacity curve at the set viewpoint and an opacity value in the opacity curve at the base viewpoint corresponding to a same voxel value does not exceeds the set tolerable amount of change. In such a case, when virtual endoscopic images are generated and displayed while a viewpoint position is sequentially changed, it is possible to display the images in such a manner that they are smoothly connected to each other. Therefore, it is possible to provide virtual endoscopic images more appropriate for observation of a tubular organ.

DESCRIPTION OF THE PREFERRED EMBODIMENTS

Figure 1:
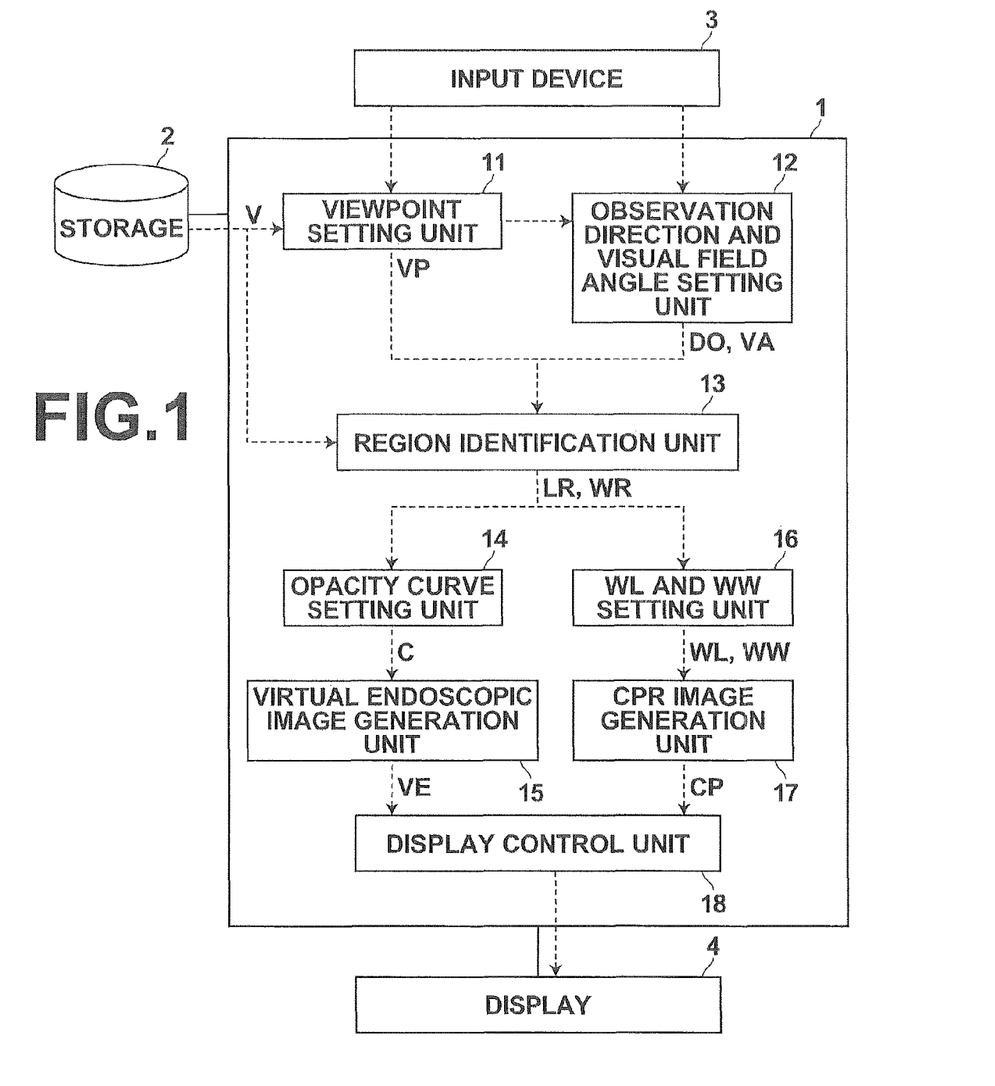
FIG. 1 is a schematic diagram illustrating the configuration of an image processing apparatus according to an embodiment of the present invention.

Hereinafter, embodiments of an image processing apparatus, method and program of the present invention will be described. FIG. 1 is a schematic diagram illustrating the configuration of an image processing apparatus 1 realized by installing an image processing program of the present invention in a computer. The image processing apparatus 1 includes a processor and a memory, as standard computer configuration. Further, the image processing apparatus 1 includes a storage 2, such as an HDD and an SSD. Further, a display 3 and an input device 4, such as a mouse and a keyboard, are connected to the image processing apparatus 1.

An image processing program and various kinds of data referred to by the image processing program are stored in the storage 2 at the time of installation, and loaded into a memory at the time of boot-up. The image processing program defines, as processing performed by a CPU, viewpoint setting processing, observation direction and visual field angle setting processing, region identification processing, opacity curve setting processing, virtual endoscopic image generation processing, window level (WL) and window width (WW) setting processing, CPR image generation processing and display control processing. When the CPU performs each of the aforementioned processing in accordance with instructions defined in the program, a general-purpose workstation functions as a viewpoint setting unit 11, an observation direction and visual field angle setting unit 12, a region identification unit 13, an opacity curve setting unit 14, a virtual endoscopic image generation unit 15, a WL and WW setting unit 16, a CPR image generation unit 17 and a display control unit 18.

The storage 2 stores three-dimensional image V (volume data) transferred from an examination division in charge of imaging, or three-dimensional image V retrieved from a database. Three-dimensional image V may be a three-dimensional image directly output from a multi-scan CT apparatus or the like. Alternatively, three-dimensional image V may be a three-dimensional image generated by reconstructing a group of two-dimensional slice data output from a conventional CT apparatus or the like.

The image processing apparatus 1 identifies, based on a user's operation of selecting or inputting information such as a patient's ID and an examination date, which is necessary to identify a three-dimensional image, corresponding three-dimensional image V in plural three-dimensional images stored in the storage 2. Further, the image processing apparatus 1 loads the three-dimensional image V from the storage 2 into the memory, and performs processing that will be described next. Here, it is assumed that three-dimensional image V representing a bronchus or bronchi or the like has been loaded into the memory.

Figure 2:
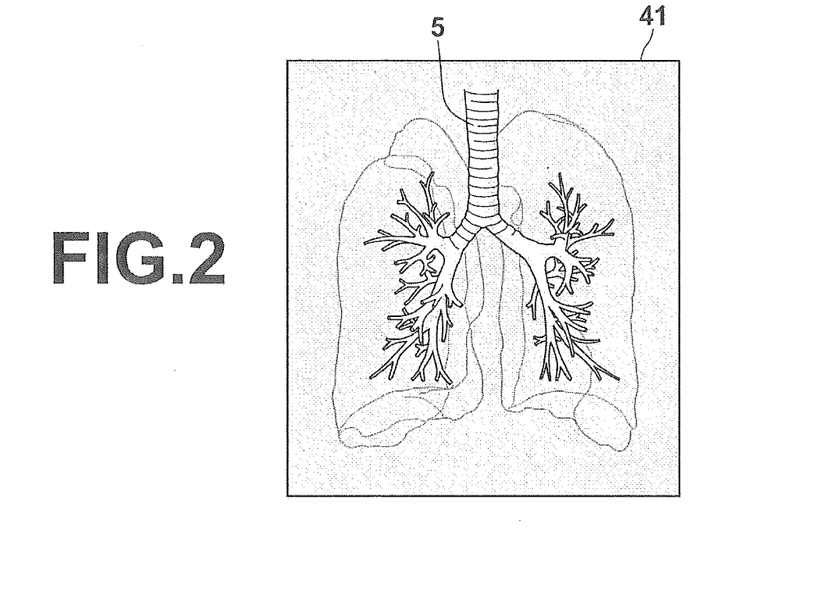
FIG. 2 is a diagram illustrating an example of an image representing a bronchus region displayed on a display.

The viewpoint setting unit 11 sets viewpoint VP of a virtual endoscopic image on the three-dimensional image V. Specifically, three-dimensional thinning processing is performed on a binary image representing a bronchus region that has been extracted by using a known technique, such as a region expansion method. Accordingly, a line passing through a central part of a bronchus or bronchi (hereinafter, referred to as a core line) is extracted. Then, an image 41 representing an extracted bronchus region 5 (or a bronchus region and a core line), for example, as illustrated in FIG. 2 is displayed on the display 3. Further, a position on core line CL corresponding to a position specified by a user is set, as viewpoint VP, based on a user's operation for specifying an arbitrary position on the bronchus region 5.

When the viewpoint setting unit 11 has received a user's operation for moving viewpoint VP, the viewpoint setting unit 11 sets viewpoint VP at a changed position that has been specified in the operation. The operation for moving viewpoint VP may be performed by operating a mouse wheel in the input device 4, or by pressing up-down arrow keys of a keyboard, or the like. Here, for example, when a wheel operation in a forward direction or an operation of pressing an up arrow key is performed, the movement direction of viewpoint VP may be the same direction (forward) as observation direction DO, which will be described later. When a wheel operation in a backward direction or an operation of pressing a down arrow key is performed, the movement direction of viewpoint VP may be an opposite direction (backward) to observation direction DO.

The observation direction and visual field angle setting unit 12 sets observation direction DO of a bronchus along the extracted core line. Further, the observation direction and visual field angle setting unit 12 sets visual field angle VA of a virtual endoscopic image. Specifically, the observation direction and visual field angle setting unit 12 obtains tree structure data representing a bronchus or bronchi by classifying, based on a relationship of connection of the core line, each voxel on the core line into an end point, an edge (edge) and a node. Further, the observation direction and visual field angle setting unit 12 sets one of an origin-side end point and a peripheral-side end point of the tree structure (for example, origin-side) as a start point, and the other end point as a terminal point. The observation direction and visual field angle setting unit 12 sets a direction along the core line from the start point toward the terminal point, as observation direction DO. Further, default value ω (for example, 120 degrees) of a visual field angle, which is set in advance and stored in the storage 2, or selected or input value ω when an operation of directly selecting or inputting a value of visual field angle is performed by a user is set, as visual field angle VA.

Figure 3:
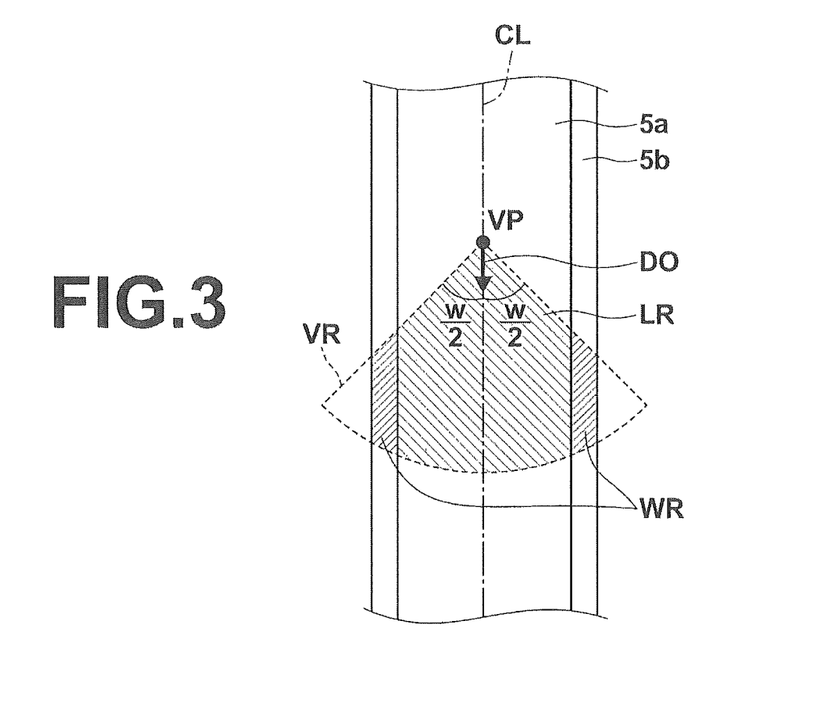
FIG. 3 is a diagram illustrating a lumen region and a wall region of a bronchus in a visual field range.

The region identification unit 13 obtains, based on the set viewpoint VP, observation direction DO and visual field angle VA, visual field range VR of a virtual endoscopic image in the three-dimensional image V. Further, the region identification unit 13 identifies each of lumen region LR and wall region WR of a bronchus or bronchi in the obtained visual field range VR. Here, visual field range VR is a fan-shaped range in predetermined size, as illustrated in FIG. 3. The fan-shaped range expands from viewpoint VP, as a vertex, at angle (ω) of visual field angle VA with respect to observation direction DO, as a center.

Specifically, each of a lumen region 5a (hereinafter, referred to as a whole lumen region) and a wall region 5b (hereinafter, referred to as a whole wall region) of a bronchus or bronchi in the whole three-dimensional image V is extracted by using a region extraction method described in B. L. Odry et al., "Active contour approach for accurate quantitative airway analysis", Medical Imaging 2008: Physiology, Function, and Structure from Medical Images, Proceedings of SPIE—Int'l, Society for Optical Engineering, Vol. 6916, pp. 691613-1-691613-11, 2008. Further, a part of the extracted whole lumen region 5a overlapping with visual field range VR is set as lumen region LR. A part of the extracted whole wall region 5b overlapping with visual field range VR is set as wall region WR (please refer to FIG. 3).

In the above document, Benjamin et al. propose a method of dividing the whole three-dimensional image into three regions of a bronchus or bronchi, i.e., a lumen region (a whole lumen region), a wall region (a whole wall region) and the other region. In the method, a first initial curve is set at a position away from a central part of a bronchus by a predetermined distance (about ½ of the diameter of a lumen) in a sectional image obtained by cutting the three-dimensional image along the core line of the bronchus. Then, the first initial curve is corrected so that a predetermined energy function that has been set in advance is minimized, and the corrected curve is used as a curve representing a boundary between the lumen of the bronchus and the wall of the bronchus. Further, a second initial curve is set at a position away from the corrected curve by a predetermined distance (about the thickness of the wall). The second initial curve is corrected so that a predetermined energy function that has been set in advance is minimized, and the corrected curve is used as a curve representing a boundary between the wall of the bronchus and a part other than the bronchus.

The opacity curve setting unit 14 obtains each of the distribution of voxel values in the identified lumen region LR and the distribution of voxel values in the identified wall region WR. Further, the opacity curve setting unit 14 sets, based on the distribution of voxel values in the regions, opacity curve C used in generation of a virtual endoscopic image, which will be described later. Specifically, the opacity curve setting unit 14 obtains a voxel value or a voxel value interval constituting a boundary between a range of voxel values in lumen region LR and a range of voxel values in wall region WR, and sets opacity curve C in which the opacity changes from a value representing a transparent state to a value representing an opaque state at the voxel value or in the voxel value interval.

Figure 4:
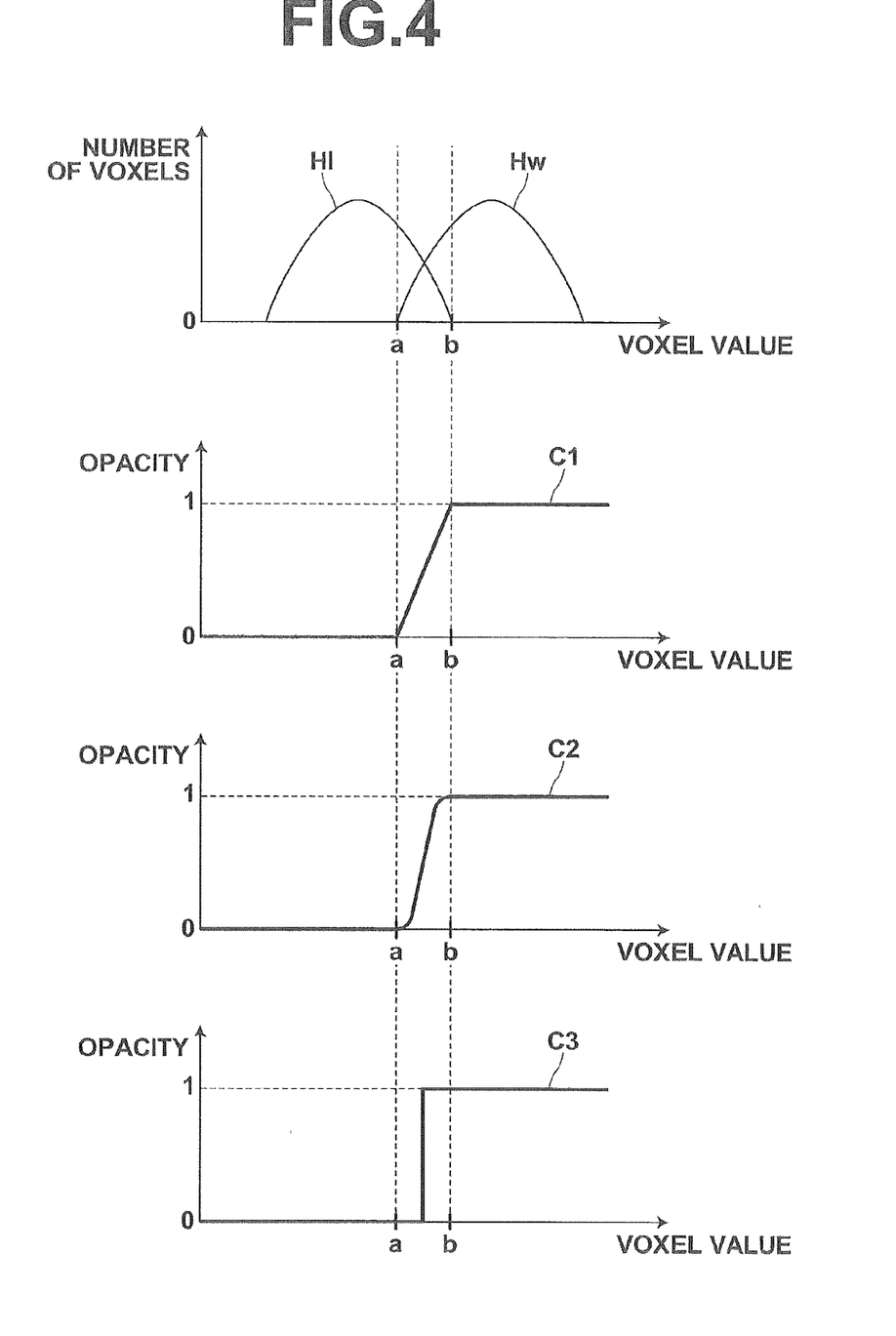
FIG. 4 is a diagram for explaining a method for setting an opacity curve based on histograms of a lumen region and a wall region.

For example, as illustrated in a graph at the top of FIG. 4, when histogram Hl of voxel values in lumen region LR and histogram Hw of voxels in wall region WR overlap with each other in voxel value interval [a,b], opacity curve C is set in such a manner that the opacity changes from "0" to a value other than "0" (for example, "1") in the voxel value interval [a,b]. For example, as illustrated in a second graph from the top of FIG. 4, opacity curve C1 in which the opacity linearly changes from the value of "0" to the value of "1" in the voxel value interval [a,b] is set.

Here, opacity curve C2, as illustrated in a third graph from the top of FIG. 4, may be set instead of opacity curve C1. In opacity curve C2, the opacity changes in a curved manner from the value of "0" to the value of "1" in the voxel value interval [a,b]. Alternatively, opacity curve C3, as illustrated in a graph at the bottom of FIG. 4, may be set. In opacity curve C3, the opacity changes stepwise from "0" to "1" at one point in the voxel value interval [a,b].

Figure 5:
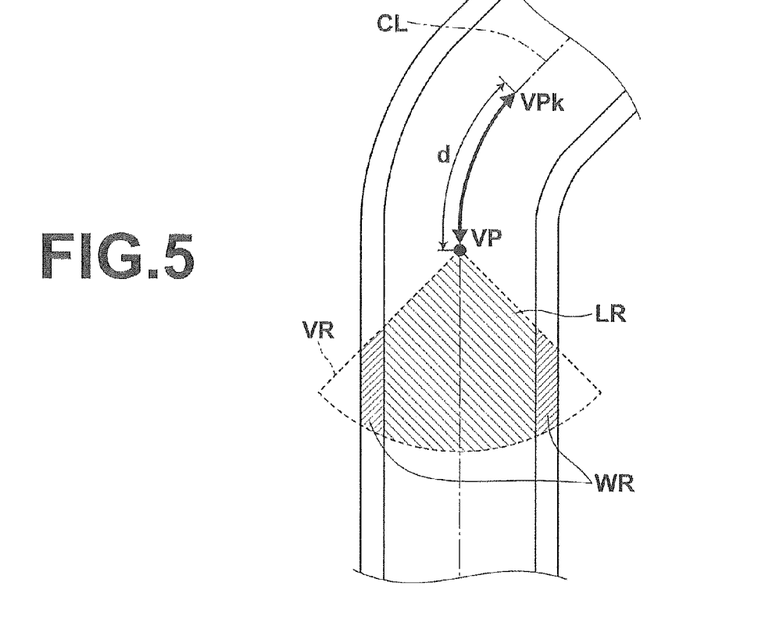
FIG. 5 is a diagram illustrating a distance, along a core line, between a set viewpoint and a base viewpoint.

Further, the opacity curve setting unit 14 has a function of storing base viewpoint VPk and opacity curve Ck at the base viewpoint VPk in advance in a memory, and setting tolerable amount k of change in opacity by using distance d (please refer to FIG. 5), along core line CL (the direction of a course of a bronchus), between the viewpoint VP that has been set by the viewpoint setting unit 11 and the base viewpoint VPk, and setting opacity curve C at viewpoint VP in such a manner that difference b between an opacity value in opacity curve C at viewpoint VP and an opacity value in opacity curve Ck at base viewpoint VPk corresponding to a same voxel value does not exceeds tolerable amount k of change. Here, tolerable amount k of change is set at a smaller value as distance d is shorter.

Base viewpoint VPk may be, for example, a viewpoint before change when the viewpoint setting unit 14 has changed the position of the viewpoint. In this case, the opacity curve setting unit 14 is configured in such a manner that a viewpoint before change and an opacity curve at the viewpoint are stored in a memory every time when the viewpoint setting unit 14 changes the viewpoint. Here, a predetermined initial viewpoint may be used as base viewpoint VPk.

Figure 6:
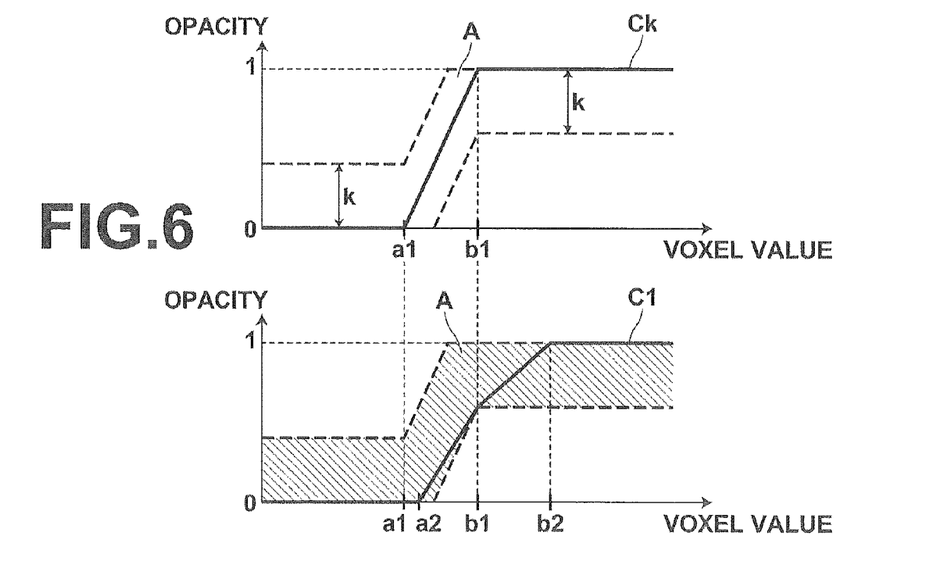
FIG. 6 is a diagram for explaining a method for setting an opacity curve in consideration of an opacity curve at a base viewpoint (No. 1)

For example, first, as illustrated in the upper diagram of FIG. 6, tolerable range A is obtained in the range of possible values of opacity, which is [0,1]. Tolerable range A has a width of tolerable amount k of change from opacity curve Ck at viewpoint VPk in the axial direction of opacity (a vertical direction in FIG. 6). Here, it is assumed that the opacity linearly changes from the value of "0" to the value of "1" in the voxel value interval [a1,b1] in opacity curve Ck. Further, as illustrated in the lower diagram of FIG. 6, opacity curve C1 is set as opacity curve C at viewpoint VP. Opacity curve C1 is determined in such a manner to lie in the obtained tolerable range A. Here, the opacity linearly changes from the value of "0" to the value of "1" in the voxel value interval [a2,b2] in opacity curve C1, and the inclination of the curve in the voxel value interval [a2,b2] is determined in such a manner that the curve lies in tolerable range A.

Instead of the aforementioned method, the opacity curve setting unit 14 may temporarily generate provisional opacity curve C2 at viewpoint VP without considering opacity curve Ck at base viewpoint VPk. After then, the opacity curve setting unit 14 may judge whether a part in which difference b between an opacity value in the generated opacity curve C2 and an opacity value in opacity curve Ck at viewpoint VPk corresponding to a same voxel value exceeds tolerable amount k of change is present or not. When it is judged that an exceeding part is not present, opacity curve C2 may be directly set as opacity curve C at viewpoint VP. When it is judged that an exceeding part is present, opacity curve C2 may be corrected so that difference b becomes less than or equal to tolerable amount k of change, and obtained opacity curve C2' after correction may be set as opacity curve C at viewpoint VP.

Figure 7:
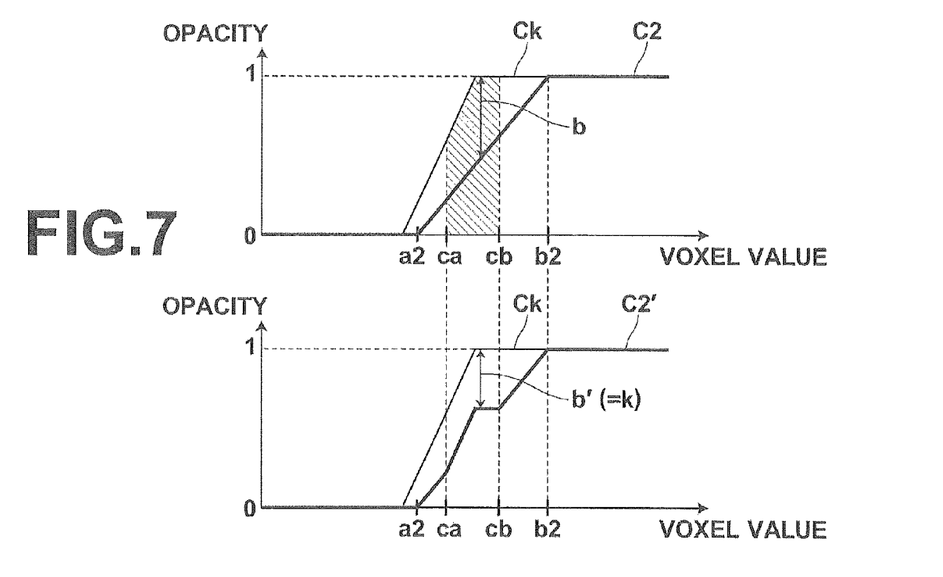
FIG. 7 is a diagram for explaining a method for setting an opacity curve in consideration of an opacity curve at a base viewpoint (No. 2)

For example, as illustrated in the upper diagram of FIG. 7, opacity curve C2, in which the opacity linearly changes from the value of "0" to the value of "1" in the voxel value interval [a2,b2], is generated as a provisional opacity curve at viewpoint VP. Then, judgment is made as to whether a part in which difference b between an opacity value in the generated opacity curve C2 and an opacity value in opacity curve Ck at viewpoint VPk corresponding to a same voxel value exceeds tolerable amount k of change is present or not. Here, it is judged that difference b between opacity values corresponding to a same voxel value exceeds tolerable amount k of change in voxel value interval [ca, cb] of opacity curve C2. Therefore, as illustrated in the lower diagram of FIG. 7, opacity curve C2 is corrected so that difference b becomes less than or equal to tolerable amount k of change, and obtained opacity curve C2' after correction is set as opacity curve C at viewpoint VP.

The virtual endoscopic image generation unit 15 generates virtual endoscopic image VE from three-dimensional image V by volume rendering using the set viewpoint VP, observation direction VO, visual field angle VA and the set opacity curve C.

The WL and WW setting unit 16 obtains the distribution of voxel values in the obtained visual field range VR. Further, the WL and WW setting unit 16 sets, based on the distribution of voxel values, window level WL and window width WW to be used to generate a CPR image, which will be described later. For example, the WL and WW setting unit 16 sets a center value in the range of voxels in visual field range VR, as window level WL, and sets ½ of the width of the range of voxel values as window width WW.

The CPR image generation unit 17 generates image CP (CPR image) representing a sectional surface of a bronchus cut along the core line of the bronchus from three-dimensional image V by using the set window level WL and window width WW, and displays image CP. There are three kinds of CPR image, namely, a projected CPR image, a stretched CPR image and a straight CPR image depending on techniques for displaying a sectional surface, as a two-dimensional plane image.

Figure 8:
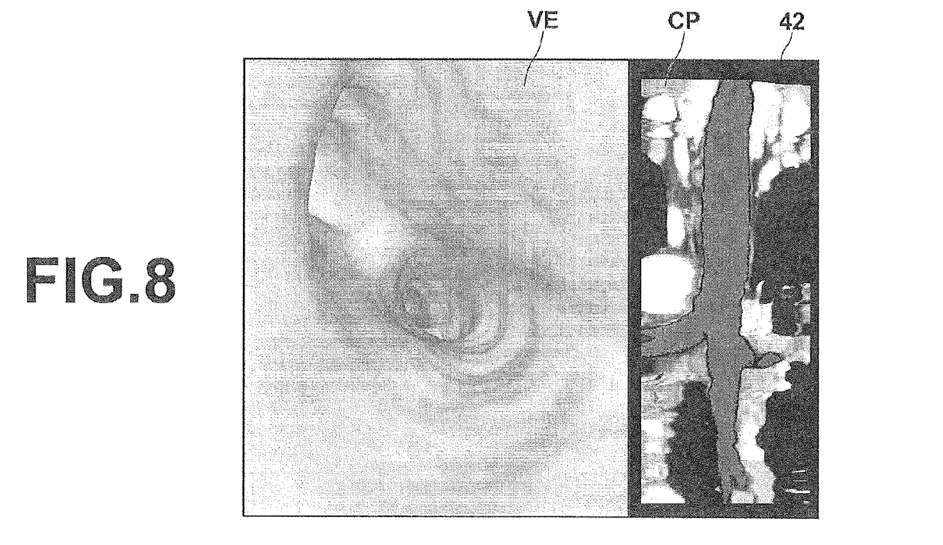
FIG. 8 is a diagram illustrating an example of a display screen displayed on a display by a display control means.

The display control unit 18 controls various kinds of display on the display 3. For example, the display control unit 18 displays virtual endoscopic image VE generated by the virtual endoscopic image generation unit 15. Alternatively, the display control unit 18 may display virtual endoscopic image VE and CPR image CP, generated by the CPR image generation unit 17, at the same time. Here, as a specific display mode, there is a mode 42 of displaying both of the images side by side, as illustrated in FIG. 8.

Further, a real endoscopic image obtained by an endoscope by imaging the inside of a bronchus within a visual field range corresponding to visual field range VR at each viewpoint corresponding to viewpoint VP set by the viewpoint setting unit 11 may be obtained. Further, the display control unit 18 may display the virtual endoscopic image VE and the real endoscopic image at the same time.

As described above, according to the embodiments of the present invention, when a virtual endoscopic image is generated from a three-dimensional image representing a tubular organ, the region identification unit 13 obtains, based on viewpoint VP, observation direction DO and visual field angle VA set by the viewpoint setting unit 11 and the observation direction and visual field angle setting unit 12, visual field range VR of the virtual endoscopic image. Further, the region identification unit 13 identifies each of lumen region LR and wall region WR of the bronchus in the obtained visual field range VR. Then, the opacity curve setting unit 14 obtains, based on histogram H1 of voxel values in lumen region LR and histogram Hw of voxel values in wall region WR, a voxel value or a voxel value interval constituting a boundary between a range of voxel values in lumen region LR and a range of voxel values in wall region WR. Further, the opacity curve setting unit 14 sets opacity curve C representing a relationship between voxel values and opacity in such a manner that the opacity changes from the value of "0" to the value of "1" at the voxel value or in the voxel value interval. Further, the virtual endoscopic image generation unit 15 generates virtual endoscopic image VE from three-dimensional image V by volume rendering using the set viewpoint VP and the set opacity curve C. Accordingly, it is possible to accurately obtain a boundary between the range of voxel values in lumen region LR and the range of voxel values in wall region WR in the vicinity of each viewpoint VP. Further, it is possible to set opacity curve C appropriate for observation of the bronchus at the viewpoint VP, and generate virtual endoscopic image VE.

The aforementioned embodiments were described by assuming that a viewpoint is located on a core line. However, it is not always necessary that the viewpoint is located on the core line. When one or both of viewpoint VP set by the viewpoint setting unit 11 and base viewpoint VPk are not located on the core line, the opacity curve setting unit 14 may obtain a corresponding point or points on the core line closest to the point or points that are not on the core line. Further, the opacity curve setting unit 14 may obtain distance d along the core line between the viewpoint VP and the viewpoint VPk by using the position or positions of the corresponding point or points, as the position of the point or the positions of the points in the bronchus.

The aforementioned embodiments were described by using a case in which the region identification unit 13 extracts each of a lumen region and a wall region of the bronchus or bronchi in the whole three-dimensional image V by using a region extraction method proposed by Benjamin, et al. However, the regions may be extracted by using other known region extraction methods, such as a region expansion method and a graph-cut method.

In the aforementioned embodiment, a bronchus or bronchi were used as an example of a tubular structure. Alternatively, a stomach, a trachea, a large intestine and the like may be a target.

What is claimed is:

1. An image processing apparatus that generates a virtual endoscopic image from a three-dimensional image representing a tubular organ, the apparatus comprising:

a viewpoint setting unit that sets viewpoints at different positions in a lumen region of the tubular organ;

a region identification unit that sets, in the three-dimensional image, a predetermined range in a vicinity of each of the set viewpoints, and identifies each of the lumen region of the tubular organ in the set range and a wall region of the tubular organ in the set range;

an opacity curve setting unit that obtains, based on information about voxel values in the identified lumen region and information about voxel values in the identified wall region, a voxel value or a voxel value interval constituting a boundary between a range of voxel values in the identified lumen region and a range of voxel values in the identified wall region, and sets an opacity curve representing a relationship between voxel values and an opacity in such a manner that the opacity changes from a value representing a transparent state to a value representing an opaque state at the voxel value or in the voxel value interval, wherein the opacity curve is set for each of the set viewpoints; and a virtual endoscopic image generation unit that generates the virtual endoscopic image for each of the set viewpoints from the three-dimensional image by volume rendering using the set opacity curve for each of the set viewpoints, wherein the predetermined range comprises a visual field range determined based on each of the set viewpoints, an observation direction and a visual field angle, and wherein the opacity curve setting unit stores a base viewpoint and an opacity curve at the base viewpoint, and sets a tolerable amount of change in opacity in such a manner that the tolerable amount is smaller as a distance, along the direction of a course of the tubular organ, between each of the set viewpoints and the base viewpoint is shorter, and sets an opacity curve at each of the set viewpoints in such a manner that a difference between an opacity value in the opacity curve at each of the set viewpoints and an opacity value in the opacity curve at the base viewpoint corresponding to a same voxel value does not exceed the set tolerable amount of change.

2. The image processing apparatus, as defined in claim 1, further comprising:
a CPR image generation unit that sets, based on voxel values in the predetermined range, a window level and a window width, and generates a CPR image representing the tubular organ from the three-dimensional image by using the set window level and window width.

3. The image processing apparatus, as defined in claim 1, wherein the opacity curve is reset each time each of the set viewpoints is moved.

4. The image processing apparatus, as defined in claim 1, wherein the opacity curve setting unit stores a base viewpoint and an opacity curve at the base viewpoint.

5. An image processing method for generating a virtual endoscopic image from a three-dimensional image representing a tubular organ, wherein the method performs, by at least one computer:
setting viewpoints at different positions in a lumen region of the tubular organ;
setting, in the three-dimensional image, a predetermined range in a vicinity of each of the set viewpoints, and identifying each of the lumen region of the tubular organ in the set range and a wall region of the tubular organ in the set range;
obtaining, based on information about voxel values in the identified lumen region and information about voxel values in the identified wall region, a voxel value or a voxel value interval constituting a boundary between a range of voxel values in the identified lumen region and a range of voxel values in the identified wall region, and setting an opacity curve representing a relationship between voxel values and opacity in such a manner that the opacity changes from a value representing a transparent state to a value representing an opaque state at the voxel value or in the voxel value interval, wherein the opacity curve is set for each of the set viewpoints; and
generating the virtual endoscopic image for each of the set viewpoints from the three-dimensional image by volume rendering using the set opacity curve for each of the set viewpoints,
wherein the predetermined range comprises a visual field range determined based on each of the set viewpoints, an observation direction and a visual field angle, and
wherein the setting the opacity curve stores a base viewpoint and an opacity curve at the base viewpoint, and sets a tolerable amount of change in opacity in such a manner that the tolerable amount is smaller as a distance, along the direction of a course of the tubular organ, between each of the set viewpoints and the base viewpoint is shorter, and sets an opacity curve at each of the set viewpoints in such a manner that a difference between an opacity value in the opacity curve at each of the set viewpoints and an opacity value in the opacity curve at the base viewpoint corresponding to a same voxel value does not exceed the set tolerable amount of change.

6. The image processing method, as defined in claim 5, wherein the method further performs:
setting, based on voxel values in the predetermined range, a window level and a window width, and generating a CPR image representing the tubular organ from the three-dimensional image by using the set window level and window width.

7. A non-transitory computer-readable recording medium having stored therein an image processing program for generating a virtual endoscopic image from a three-dimensional image representing a tubular organ, the program causing a computer to function as:
a viewpoint setting unit that sets viewpoints at different positions in a lumen region of the tubular organ;
a region identification unit that sets, in the three-dimensional image, a predetermined range in a vicinity of each of the set viewpoints, and identifies each of the lumen region of the tubular organ in the set range and a wall region of the tubular organ in the set range;
an opacity curve setting unit that obtains, based on information about voxel values in the identified lumen region and information about voxel values in the identified wall region, a voxel value or a voxel value interval constituting a boundary between a range of voxel values in the identified lumen region and a range of voxel values in the identified wall region, and sets an opacity curve representing a relationship between voxel values and opacity in such a manner that the opacity changes from a value representing a transparent state to a value representing an opaque state at the voxel value or in the voxel value interval, wherein the opacity curve is set for each of the set of viewpoints; and
a virtual endoscopic image generation unit that generates the virtual endoscopic image for each of the set of viewpoints from the three-dimensional image by volume rendering the set opacity curve for each of the set viewpoints,
wherein the predetermined range comprises a visual field range determined based on each of the set viewpoints, an observation direction and a visual field angle, and
wherein the opacity curve setting unit stores a base viewpoint and an opacity curve at the base viewpoint, and sets a tolerable amount of change in opacity in such a manner that the tolerable amount is smaller as a distance, along the direction of a course of the tubular organ, between each of the set viewpoints and the base viewpoint is shorter, and sets an opacity curve at each of the set viewpoints in such a manner that a difference between an opacity value in the opacity curve at each of the set viewpoints and an opacity value in the opacity curve at the base viewpoint corresponding to a same voxel value does not exceed the set tolerable amount of change.

8. The non-transitory computer-readable recording medium, as defined in claim 7, wherein the predetermined range comprises a visual field range determined based on each of the set viewpoints, an observation direction and a visual field angle.

9. An image processing apparatus that generates a virtual endoscopic image from a three-dimensional image representing a tubular organ, the apparatus comprising:
a viewpoint setting unit that sets viewpoints at different positions in a lumen region of the tubular organ;
a region identification unit that sets, in the three-dimensional image, a predetermined range in a vicinity of each of the set viewpoints, and identifies each of the lumen region of the tubular organ in the set range and a wall region of the tubular organ in the set range;

an opacity curve setting unit that obtains, based on information about voxel values in the identified lumen region and information about voxel values in the identified wall region, a voxel value or a voxel value interval constituting a boundary between a range of voxel values in the identified lumen region and a range of voxel values in the identified wall region, and sets an opacity curve representing a relationship between voxel values and an opacity in such a manner that the opacity changes from a value representing a transparent state to a value representing an opaque state at the voxel value or in the voxel value interval, wherein the opacity curve is set for each of the set viewpoints; and a virtual endoscopic image generation unit that generates the virtual endoscopic image for each of the set viewpoints from the three-dimensional image by volume rendering using the set opacity curve for each of the set viewpoints, wherein the opacity curve setting unit stores a base viewpoint and an opacity curve at the base viewpoint, and sets a tolerable amount of change in opacity in such a manner that the tolerable amount is smaller as a distance, along the direction of a course of the tubular organ, between each of the set viewpoints and the base viewpoint is shorter.

10. An image processing apparatus that generates a virtual endoscopic image from three-dimensional image representing a tubular organ, the apparatus comprising:

a viewpoint setting unit that sets viewpoints at different positions in a lumen region of the tubular organ;

a region identification unit that sets, in the three-dimensional image, a predetermined range in a vicinity of each of the set viewpoints, and identifies each of the lumen region of the tubular organ in the set range and a wall region of the tubular organ in the set range;

an opacity curve setting unit that obtains, based on information about voxel values in the identified lumen region and information about voxel values in the identified wall region, a voxel value or a voxel value interval constituting a boundary between a range of voxel values in the identified lumen region and a range of voxel values in the identified wall region, and sets an opacity curve representing a relationship between voxel values and an opacity in such a manner that the opacity changes from a value representing a transparent state to a value representing an opaque state at the voxel value or in the voxel value interval, wherein the opacity curve is set for each of the set viewpoints; and a virtual endoscopic image generation unit that generates the virtual endoscopic image for each of the set viewpoints from the three-dimensional image by volume rendering using the set opacity curve for each of the set viewpoints, wherein the opacity curve setting unit stores a base viewpoint and an opacity curve at the base viewpoint, and sets an opacity curve at each of the set viewpoints in such a manner that a difference between an opacity value in the opacity curve at each of the set viewpoints and an opacity value in the opacity curve at the base viewpoint corresponding to a same voxel value does not exceed the set tolerable amount of change.

11. A non-transitory computer-readable recording medium having stored therein an image processing program for generating a virtual endoscopic image from a three-dimensional image representing a tubular organ, the program causing a computer to function as:

a viewpoint setting unit that sets viewpoints at different positions in a lumen region of the tubular organ;

a region identification unit that sets, in the three-dimensional image, a predetermined range in a vicinity of each of the set viewpoints, and identifies each of the lumen region of the tubular organ in the set range and a wall region of the tubular organ in the set range;

an opacity curve setting unit that obtains, based on information about voxel values in the identified lumen region and information about voxel values in the identified wall region, a voxel value or a voxel value interval constituting a boundary between a range of voxel values in the identified lumen region and a range of voxel values in the identified wall region, and sets an opacity curve representing a relationship between voxel values and an opacity in such a manner that the opacity changes from a value representing a transparent state to a value representing an opaque state at the voxel value or in the voxel value interval, wherein the opacity curve is set for each of the set viewpoints; and a virtual endoscopic image generation unit that generates the virtual endoscopic image for each of the set viewpoints from the three-dimensional image by volume rendering using the set opacity curve for each of the set viewpoints, wherein the opacity curve setting unit stores a base viewpoint and an opacity curve at the base viewpoint, and sets a tolerable amount of change in opacity in such a manner that the tolerable amount is smaller as a distance, along the direction of a course of the tubular organ, between each of the set viewpoints and the base viewpoint is shorter.

12. A non-transitory computer-readable recording medium having stored therein an image processing program for generating a virtual endoscopic image from a three-dimensional image representing a tubular organ, the program causing a computer to function as:

a viewpoint setting unit that sets viewpoints at different positions in a lumen region of the tubular organ;

a region identification unit that sets, in the three-dimensional image, a predetermined range in a vicinity of each of the set viewpoints, and identifies each of the lumen region of the tubular organ in the set range and a wall region of the tubular organ in the set range;

an opacity curve setting unit that obtains, based on information about voxel values in the identified lumen region and information about voxel values in the identified wall region, a voxel value or a voxel value interval constituting a boundary between a range of voxel values in the identified lumen region and a range of voxel values in the identified wall region, and sets an opacity curve representing a relationship between voxel values and an opacity in such a manner that the opacity changes from a value representing a transparent state to a value representing an opaque state at the voxel value or in the voxel value interval, wherein the opacity curve is set for each of the set viewpoints; and a virtual endoscopic image generation unit that generates the virtual endoscopic image for each of the set viewpoints from the three-dimensional image by volume rendering using the set opacity curve for each of the set viewpoints, wherein the opacity curve setting unit stores a base viewpoint and an opacity curve at the base viewpoint, and sets an opacity curve at each of the set viewpoints in such a manner that a difference between an opacity value in the opacity curve at each of the set viewpoints and an opacity value in the opacity curve at the base viewpoint corresponding to a same voxel value does not exceed the set tolerable amount of change.

13. An image processing method for generating a virtual endoscopic image from a three-dimensional image representing a tubular organ, wherein the method performs, by at least one computer:

setting viewpoints at different positions in a lumen region of the tubular organ;

setting, in the three-dimensional image, a predetermined range in a vicinity of each of the set viewpoints, and identifying each of the lumen region of the tubular organ in the set range and a wall region of the tubular organ in the set range;

obtaining, based on information about voxel values in the identified lumen region and information about voxel values in the identified wall region, a voxel value or a voxel value interval constituting a boundary between a range of voxel values in the identified lumen region and a range of voxel values in the identified wall region, and setting an opacity curve representing a relationship between voxel values and opacity in such a manner that the opacity changes from a value representing a transparent state to a value representing an opaque state at the voxel value or in the voxel value interval, wherein the opacity curve is set for each of the set viewpoints; and generating the virtual endoscopic image for each of the set viewpoints from the three-dimensional image by volume rendering using the set opacity curve for each of the set viewpoints;

storing a base viewpoint and an opacity curve at the base viewpoint; and setting a tolerable amount of change in opacity in such a manner that the tolerable amount is smaller as a distance, along the direction of a course of the tubular organ, between each of the set viewpoints and the base viewpoint is shorter.

14. An image processing method for generating a virtual endoscopic image from a three-dimensional image representing a tubular organ, wherein the method perfon is, by at least one computer:

setting viewpoints at different positions in a lumen region of the tubular organ;

setting, in the three-dimensional image, a predetermined range in a vicinity of each of the set viewpoints, and identifying each of the lumen region of the tubular organ in the set range and a wall region of the tubular organ in the set range;

obtaining, based on information about voxel values in the identified lumen region and information about voxel values in the identified wall region, a voxel value or a voxel value interval constituting a boundary between a range of voxel values in the identified lumen region and a range of voxel values in the identified wall region, and setting an opacity curve representing a relationship between voxel values and opacity in such a manner that the opacity changes from a value representing a transparent state to a value representing an opaque state at the voxel value or in the voxel value interval, wherein the opacity curve is set for each of the set viewpoints; and generating the virtual endoscopic image for each of the set viewpoints from the three-dimensional image by volume rendering using the set opacity curve for each of the set viewpoints;

storing a base viewpoint and an opacity curve at the base viewpoint;

setting an opacity curve at each of the set viewpoints in such a manner that a difference between an opacity value in the opacity curve at each of the set viewpoints and an opacity value in the opacity curve at the base viewpoint corresponding to a same voxel value does not exceed the set tolerable amount of change.

* * * * *

UNITED STATES PATENT AND TRADEMARK OFFICE
CERTIFICATE OF CORRECTION

PATENT NO.         : 9,530,238 B2                                    Page 1 of 1
APPLICATION NO.    : 14/289542
DATED              : December 27, 2016
INVENTOR(S)        : Inoue It is certified that error appears in the above-identified patent and that said Letters Patent is hereby corrected as shown below:

On the Title Page

In (71) Applicant: please replace "Tokyo (KR)" with "Tokyo (JP)" and
In (72) Inventor: please replace "Tokyo (KR)" with "Tokyo (JP)".

Signed and Sealed this
Fourteenth Day of March, 2017

Michelle K. Lee
*Director of the United States Patent and Trademark Office*